United States Patent [19]
Futami et al.

[11] Patent Number: 5,203,914
[45] Date of Patent: Apr. 20, 1993

[54] DENTAL COMPOSITION FOR IMPRESSION-TAKING

[75] Inventors: Shunichi Futami, Nagareyama; Hiroshi Kamohara, Tokyo, both of Japan

[73] Assignee: GC Corporation, Tokyo, Japan

[21] Appl. No.: 712,425

[22] Filed: Jun. 10, 1991

[30] Foreign Application Priority Data

Jun. 11, 1990 [JP] Japan .................................. 2-149888

[51] Int. Cl.$^5$ ............................................. C09K 3/00
[52] U.S. Cl. ...................................... 106/35; 523/109
[58] Field of Search ............................................. 106/35

[56] References Cited

U.S. PATENT DOCUMENTS 4,708,821 11/1987 Shimokawa et al. ................. 512/12

FOREIGN PATENT DOCUMENTS 58-59263 12/1982 Japan .
61-21171 1/1986 Japan .

*Primary Examiner*—Mark L. Bell
*Assistant Examiner*—Margaret Einsmann
*Attorney, Agent, or Firm*—Oblon, Spivak, McClelland, Maier & Neustadt

[57] ABSTRACT

A dental impression composition which contains as a main component 4 to 40% by weight of an acetoacetylated polyvinyl alcohol having an acetoacetylation degree of 0.5 to 15 mol % and a polymerization degree of 100 to 1,500, and additional components 1 to 20% by weight of gelling agents and 20 to 85% by weight of fillers.

9 Claims, No Drawings

DENTAL COMPOSITION FOR IMPRESSION-TAKING

BACKGROUND OF THE INVENTION

1. Field of the Invention

The present invention relates to a dental composition for intra-oral impression-material, which is provided in such a powdery or pasty form that, when in the powdery form, it forms an aqueous gel upon being mixed with water, or when in a two-pack paste form, it gels upon mixing. This dental composition is characterized in that it is much superior in storage stability, dimensional stability and accuracy to analogous alginate impression materials and is virtually unreactive with the surfaces of gypsum models.

2. Prior Art

Dental impression materials are generally broken down into non-elastic and elastic types; dental impression materials of this invention belongs to the latter type. Impression materials so far used are based on agar, alginates, polysulfide rubber, polyether, silicone rubber and the like.

The elastic impression material, even when having deformed elastically in removing the impression from the oral cavity, tends to revert to its original form in the absence of stress. Thus, it can be used to take impressions of the teeth, row of teeth, jaw, mucosa and other intra-oral regions, all being morphologically complicated due to the presence of undercuts.

Synthetic rubber-based impression materials formed of such kinds of rubber as polysulfide rubber, polyether rubber and silicone rubber have the properties of being clinically moderate in elasticity, easy to manipulate and low in permanent deformation as well as being reduced or limited in the dimensional change with time and tensile strength of their set products, and so have been used to take precise impressions.

However, the polysulfide rubber impression material is disadvantageous in that it gives off unpleasant smells and is slow-setting, while the polyether rubber impression material has the defects of being not only hard and lower in rubber elasticity but is noticeably affected by moisture as well, though not so much affected as the alginate material. Silicone rubber, by contrast, is now considered the most suitable material for precise impression-taking, because it is tasteless and odorless, sharply set, excellent in elastic properties, extremely limited in dimensional change and improved in dimensional stability. However, the drawback of it is that it is expensive. By and large, such synthetic rubber-based impression materials have a major defect of being costly. Consequently, most dental clinics still rely upon agar and alginate impression materials for such limited purposes as taking one-point impressions for crowns or inlays and general impressions. This is because in spite of their defects of being larger in permanent deformation, richer in moisture so that the resulting impressions can undergo larger dimensional changes with time, and lower in tensile strength so that the resulting impressions can tear up easily, as compared with the synthetic rubber-based impression materials, they are much richer in hydrophilic nature and elasticity so that impression-taking can be facilitated, and, particularly, they are available at low cost. In Japan in particular, agar-alginate combination impressions enjoy increased use.

Among them, the alginate impression material, now used most abundantly, is provided mainly in a powdery form and is designed to gel when mixed with water. In recent years, low-dusting, powdery alginate impression material has been used with a view to improving dental work and working environments. Rendering it completely dust-free, however, is still unfeasible.

For use, given amounts of the powdery alginate impression material and water are kneaded together in a small rubber bowl with the use of a spatula to prepare a paste, which is then inserted into and brought into pressure contact with the oral cavity through an impression tray. After the paste gels into an elastomer, it is removed from within the mouth to take the intra-oral impression. After that, gypsum slurry is poured in the negative-die of the impression to make a working model for preparing prostheses, thereby making a gypsum model. How faithfully the surface details of the gypsum model are reproduced is correlated with the degree that the prepared prosthesis is fitted into the oral cavity. The surface roughness of the gypsum model is then governed by the affinity between or the interfacial relation between the alginate impression material and the gypsum model. For this reason, it is practically of crucial importance to use selectively material that promotes or accelerates the gelation of the alginate impression but does not inhibit, the hardening of gypsum.

As explained above, although the alginate impression material is inexpensive, it is poor in tensile strength and renders the surface roughness of the gypsum model large. For all the numerous studies so far made to eliminate such defects, no satisfactory alginate impression material has yet been developed.

The rubbery impression materials are lower in their dimensional change with time and satisfactory in terms of tensile strength and the roughness of the gypsum model surface, on the other hand, there is a limitation to slashing the cost in consideration of their starting materials themselves being costly. It would thus be impossible to make them comparable to alginate in terms of price.

There is thus a great demand toward an impression material which is as inexpensive as the alginate impression material, and is as low in dimensional change with time and is as satisfactory in terms of tensile strength and roughness of a gypsum model surface as the rubbery impression material.

SUMMARY OF THE INVENTION

We have successfully developed a novel impression material comprising an acetoacetylated polyvinyl alcohol, reactants or gelling agents, filler materials and water which gel upon being mixed together. This impression material is provided in a paste or powdery form. In the paste form, it consists of Material A and Material B which are designed to gel upon being mixed and kneaded together. More illustratively, Material A comprises an acetoacetylated polyvinyl alcohol, fillers and water, while Material B comprises gelling agents, fillers and water. The powdery material is designed to gel by mixing water with a powder component that is a mixture of an acetoacetylated polyvinyl alcohol, a gelling agent and a filler.

The impression material according to this invention can provide an unprecedentedly novel, precise impression material which is much more inexpensive than the rubbery impression ones, and is even higher in tensile strength, lower in dimensional change and lower in terms of the surface roughness of the resulting gypsum model, when compared with the alginate one.

DETAILED EXPLANATION OF THE INVENTION

In the first place, the constituents of the composition according to this invention will be explained in greater detail.

The acetoacetylated PVA is known to have a large influence on gel formation depending upon its degree of acetoacetylation. In other words, a polyvinyl alcohol with an acetoacetylation degree less than 0.5 mol % is not useful for dental impression materials due to its ability to form gel being very slim. A polyvinyl alcohol having an acetoacetylation degree higher than 15 mol % is again unsuitable for impression-taking, since it is so low in solubility in water that its gelation with water is difficult, failing to produce any aqueous gel. Thus, the acetoacetylation degree of the PVA usable for dental impressions should preferably be limited to the range of 0.5 to 15 mol %.

Acetoacetylated PVA, whose degrees of polymerization are less than 100 or more than 1500, are all impractical because the former are unable to afford sufficient strength to the resulting gel, whereas the latter are slow in the rate of dissolution in water and much less sensitive to gelation. Thus, the polymerization degree of the acetoacetylated PVA usable for dental impression materials should preferably lie in the range of 100 to 1500.

In order for the acetoacetylated PVA to provide a suitable aqueous gel, its amount must lie in the range of 4 to 40% by weight for powder systems and 2 to 20% by weight for two-pack paste systems. If the powder system contains the acetoacetylated PVA in amounts less than 4% by weight, the gel obtained by mixing with water will then be unsuitable for impression materials due to its decreased strength. In quantities of more than 40% by weight, the resulting gel will be impractical because of difficulty encountered in forming it into a uniform paste with water. If the two-pack paste system contains the acetoacetylated PVA in amounts of less than 2% by weight, the resulting gel will then be unsuitable for impression materials due to its decreased strength. In quantities exceeding 20% by weight, the resulting gel will not dissolve in water, thus giving rise to precipitates.

Preferable as the gelling agents, for instance, are compounds containing aldehyde and dialdehyde groups, hydrazide group-containing compounds, diamine compounds, polyamine compounds and amino acids.

The amount of the gelling agent used differs depending upon whether it is used with the powder or two-pack paste system.

If the powder system contains the gelling agent in too small an amount—less than 1% by weight, the resulting gel will then become impractical due to its decreased strength. In too large a quantity—exceeding 20% by weight, the surface smoothness of the resulting gypsum model will be rapidly lost due to an excessive portion of the gelling agent. Thus, the amount of the gelling agent to be contained should be restricted to the range of 1 to 20% by weight.

If the two-pack paste system contains the gelling agent in too small an amount—less than 0.5% by weight, the resulting gel will then become impractical due to its decreased strength. In too large a quantity—exceeding 15% by weight, the surface smoothness of the resulting gypsum model will be rapidly lost due to an excessive portion of the gelling agent. Thus, the amount of the gelling agent to be incorporated in the two-pack paste system should lie in the range of 0.5 to 15% by weight.

Among the (di)aldehyde group-containing compounds taking part in reactions useful for dental impression materials, there are acetoaldehyde, propionaldehyde, crotonaldehyde, glyoxal, malonaldehyde, glutaraldehyde and dialdehyde starch. For the reaction mechanism having not yet to be clarified, it is postulated that such compounds would be crosslinked to the acetoacetyl group-containing polyvinyl alcohol to form a gel product, according to the following reaction scheme.

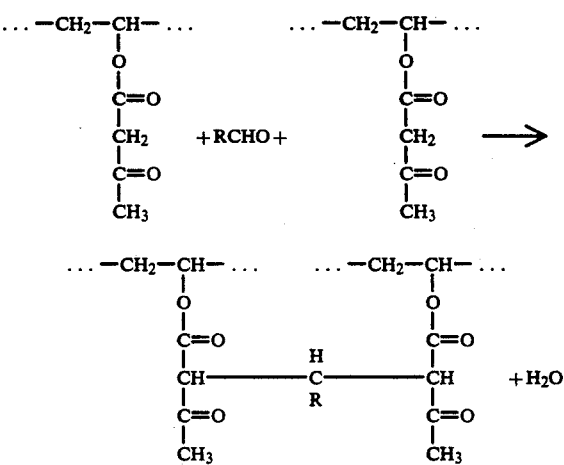

The hydrazide group-containing compounds taking part in reactions useful for dental impression materials include carbodihydrazide, oxalic dihydrazide, malonic dihydrazide, succinic dihydrazide, adipic dihydrazide, sebacic dihydrazide, dodecane dionic dihyrazide, isophthalic dihydrazide and terephthalic dihydrazide. For the reaction mechanism involved, which awaits elucidation, it is presumed that such compounds would be crosslinked to the acetoacetyl group-containing polyvinyl alcohol to form a gel product, according to the following reaction scheme.

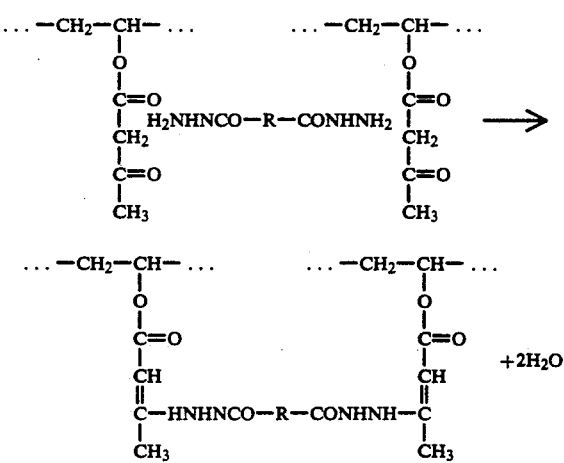

The amino group-containing compounds, for instance, include diamine compounds, polyamine compounds and amino acids. More illustratively, diethyltriamine, triethylenetetramine, menthenediamine, isophoronediamine, a polyethylene-imine having a molecular weight of 300–100,000 and represented by the following formula:

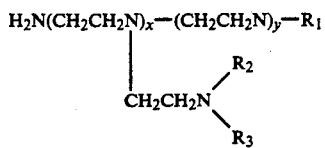

wherein $R_1$, $R_2$ and $R_3$ each stand for H or $CH_2CH_2NH_2$ and x and y are an integer, L-lysine, hydroxylysine, L-arginine and L-ornithine are useful. For the reaction mechanism involved, which has not been confirmed as yet, it is assumed that such compounds would be crosslinked to the acetoacetyl group-containing polyvinyl alcohol to form a gel product, according to the following reaction scheme.

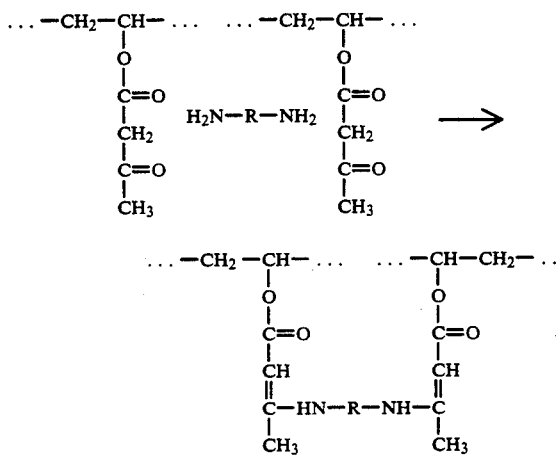

In order to promote the above-mentioned gelling reactions, they must occur at pH 7.0 or less or, in other words, in an acidic enviroment. For this reason, the filler used must be a neutral or acidic material showing a pH value of 7.0 or less, such as silica, basic aluminium sulfate, alumina and titanium oxide. In most cases, such fillers as silica contain alkaline contaminants, and so should be selected carefully. Therefore, fillers conventionally used for the alginate impression materials, such as alkaline diatomaceous earth and talc having a mean particle size of larger than 5 μm, cannot be used for this invention, since their use results in degradation of gel elasticity.

Fillers having an average particle diameter of less than 1 mμ are unsuitable due to a rapid viscosity rise and difficulty involved in kneading. Thus, the fillers used in this invention should be limited to those having an average particle diameter lying in the range of 1 mμ to 5 μm.

The filler content in powder system is different from that of two-pack paste system. If the powder system contains less than 20 weight % of the filler, the resulting gel will then become impractical due to its insufficient strength and difficulty involved in forming it into a uniform paste with water. The use of the filler in an amount exceeding 85 weight % is again unsuitable due to a serious elasticity drop. Therefore, the filler content used with the powder system should be limited to the range of 20 to 85 weight %.

If the two-pack paste system contains less than 5 weight % of the filler for each of Materials A and B, the resulting gel will then become unsuitable due to its insufficient strength. If it contains more than 60% by weight of the filler for each of Materials A and B, the resulting gel will again become unsuitable for a serious shortage of elasticity. The amount of the filler to be incorporated in the two-pack paste system should, therefore, be restricted to the range of 5 to 60% by weight for each of Materials A and B.

For a better understanding of this invention, it is noteworthy to summarize what the inventive material is composed of:

(1) A mixture of a PVA having an acetoacetylation degree of 0.5 to 15 mol % and a polymerization degree of 100 to 1,500, gelling agents and fillers, all in a powdery form, are stirred with and dissolved in an appropriate ratio of water to form an aqueous gel product at room temperature, which is used for dental impression-taking.

(2) Even when one of Materials A and B is in an aqueous solution or pasty form and the other in a powdery form, it is possible to obtain an aqueous gel at room temperature by mixing and stirring them, which is then used for impression-taking.

(i) Material A: Acetoacetylated PVA (hereinafter APVA for short) in an aqueous solution form.

Material B: Powdery composition comprising one or more gelling agents selected from the compounds consisting of aldehyde-, dialdehyde-, hydrazide- or amino-group (diamine, polyamine and amino acid) and filler.

(ii) Material A: Pasty composition in which APVA and filler are added to water.

Material B: Powdery composition to which added are one or more gelling agents selected from the compounds consisting of aldehyde-, dialdehyde-, hydrazide- or amino-group (diamine, polyamine and amino acid) and fillers if necessary.

Suitable amounts of Materials A and B are mixed together into an aqueous gel at room temperature, which is in turn used for impression-taking.

(3) Material A—Paste composition comprising:
APVA,
Filler (having a pH value of 7.0 or less and a mean particle size of 1 mμ to 5 μm), and
Water.

Material B—Paste composition comprising:
One or more gelling agents selected from the compounds consisting of aldehyde-, dialdehyde-, hydrazide-, amino-group,
Filler (having a pH value of 7.0 or less and a mean particle size of 1 mμ to 5 μm), and
Water.

Suitable amounts of Materials A and B are mixed together into an aqueous gel product at room temperature, which is in turn used for impression-taking.

Additionally and optionally, colorants and aromatizing agents are added to (1), (2) or (3). The colorants may be those normally used with the alginate impression materials, while the aromatizing agents may be usual ones. In this regard, the present invention is not critical.

Moreover, a paste-paste type of materials may be kneaded within a short period of time with the use of mixing equipment.

Unlike the alginate impression material, the unprecedented dental impression material based of APVA according to this invention experiences little or no degradation by heat, light, air or other factors—because this is a synthetic, not naturally occurring, product, and has much more improved storage stability. Such properties have been found for the first time by the present inventors.

The inventive material is also superior to the alginate impression material in terms of water retention and dimensional stability. In addition, this is not virtually affected by antiseptics and fits well to a gypsum surface.

Thus, the inventive composition, although unprecedentedly novel in a sense of its having such properties as not found in conventional hydraulic dental impression materials, provides successfully a very unique impression material.

EXAMPLES

The present invention will now be explained more specifically and illustratively, but not exclusively, with reference to the following examples.

EXAMPLE 1

| | |
|---|---|
| APVA (having an acetoacetylation degree of 7.5 mol % and a polymerization degree of 200) | 14 wt. % |
| Carbodihydrazide | 2 wt. % |
| Finely divided silica ("Nipsil NS", brandname, made by Nippon Silica Kogyo K.K. and having a mean particle size of 40 mμ and a pH value of 5.5) | 84 wt. % |

These three components were mixed together for 30 minutes in a mixing machine. The resulting uniform powders, in a weighed amount of 10 g, were kneaded with 40 g of tap water for 2 minutes in a small rubber bowl with the use of an exclusive spatula. The obtained homogeneous paste gelled after ten minutes. The tensile strength was about three times as great as that of an alginate impression material. Following obtaining a mold with a glass plane, an α-type of gypsum ("New Plastone", brandname, made by GC Dental Industrial Corp.) was cast in the mold for setting. The set product was found to have a ten points average surface roughness of 7.5 μm, indicating that the obtained gypsum surface was smoother than that of a control alginate impression material.

EXAMPLE 2

| | |
|---|---|
| APVA (having an acetoacetylation degree of 1 mol % and a polymerization degree of 1100) | 38 wt. % |
| Glutaraldehyde | 14 wt. % |
| Isophthalic dihydrazide | 18 wt. % |
| Basic aluminium sulfate ("Alumina White" brandname, and having a mean particle size of 5 μm and a pH value of 4) | 30 wt. % |

These four components were sufficiently mixed together for 40 minutes in a mixing machine. The resulting uniform powders, in a weighed amount of 6 g, were kneaded with 40 g of tap water for two minutes in a small rubber bowl with the use of an exclusive spatula. The obtained homogeneous paste gelled after eight minutes. The tensile strength was about 2.8 times as great as that of an alginate impression material. Following obtaining a mold with a glass plane, an α-type of gypsum ("New Plastone", brandname, made by GC Dental Industrial Corp.) was cast in the mold for setting. The set gypsum product was found to have a ten-point average surface roughness of 6.5 μm, indicating that the obtained gypsum surface were smoother than that of a control alginate impression material.

EXAMPLE 3

| Material A: | |
|---|---|
| APVA (having an acetoacetylation degree of 14 mol % and a polymerization degree of 500) | 2 wt. % |
| Finely divided silica ("Nipsil N-300A", brandname, made by Nippon Silica Kogyo K.K. and having a mean particle size of 2 mμ and a pH value of 6.0) | 22 wt. % |
| Distilled water | 76 wt. % |

In a kneader, APVA was dissolved under agitation in the prescribed amount of distilled water for 5 minutes. After that, the given amount of "Nipsil N-300A" was well kneaded with the resulting solution for 30 minutes to form a homogeneous paste.

| Material B: | |
|---|---|
| Propionaldehyde | 4 wt. % |
| Carbodialdehyde | 2 wt. % |
| L-lysine | 8 Wt. % |
| Finely divided silica ("Mizukasil P-526N", brandname, made by Mizusawa Kagaku Kogyo K.K. and having a mean particle size of 4 μm and a pH value of 6.7) | 12 Wt. % |
| Distilled water | 74 wt. % |

In a kneader, the first three components were well dissolved under stirring in the given amount of distilled water for ten minutes. After that, the predetermined amount of "Mizukasil P-526N" was well kneaded with the resulting solution for 40 minutes to obtain a homogeneous paste.

Materials A and B, each in a weighed amount of 10 g, were kneaded in a small rubber bowl for 30 minutes with the use of an exclusive spatula. The resulting homogeneous paste gelated after 9 minutes. The tensile strength was about 2.5 times as great as that of an alginate impression material. Following obtaining a mold with a glass plane, an α-type of gypsum ("New Plastone", brandname, made by GC Dental Industrial Corp.) was cast in the mold for setting. The set gypsum product was found to have a ten-point average surface roughness of 6.0 μm, indicating that the obtained gypsum surface was smoother than that of a control alginate impression material.

EXAMPLE 4

| Material A: | |
|---|---|
| APVA (having an acetoacetylation degree of 10 mol % and a polymerization degree of 200) | 4 wt. % |
| Finely divided silica ("Carplex #80", brandname, made by Shionogi & Co., Ltd. and having a mean particle size of 50 mμ and a pH value of 6.0) | 14 wt. % |
| Distilled water | 82 wt. % |

In a kneader, APVA was dissolved under agitation in the prescribed amount of distilled water for 8 minutes. After that, the given amount of "Carplex #80" powders was well kneaded with the resulting solution for 30 minutes to form a homogeneous paste.

| Material B: | |
|---|---|
| Glyoxal | 1 wt. % |
| Oxalic dihydrazide | 1 wt. % |
| Titanium oxide ("Titanium oxide P-25", brandname, made by Nippon Aerosil K.K. and having a mean particle size of 21 mμ and a pH value of 3.5) | 45 wt. % |
| Distilled water | 53 wt. % |

In a kneader, the first two components were dissolved under stirring in the given amount of distilled water for 8 minutes. After that, the given amount of the titanium oxide powders was well kneaded with the resulting solution for 60 minutes to obtain a homogeneous paste.

Materials A and B, each in a weighed amount of 10 g, were kneaded together for 20 seconds in a mixing machine. The resulting homogeneous paste gelated after 10 minutes. The tensile strength was about 2.6 times as great as that of an alginate impression material. Following obtaining a mold with a glass plane, an α-type of gypsum ("New Plastone", brandname, made by GC Dental Industrial Corp.) was cast in the mold for setting. The set gypsum product was found to have a ten-point average surface roughness of 6.5 μm, indicating that the obtained gypsum surface was smoother than that of a control alginate impression material.

EXAMPLE 5

| Material A: | |
|---|---|
| APVA (having an acetoacetylation degree of 13 mol % and a polymerization degree of 400) | 8 wt. % |
| Finely divided silica "Siloide 978", brandname, made by Fuji Davidson Kagaku K.K. and having a mean particle size of 2.5 μm and a pH value of 2.5) | 20 wt. % |
| Pure water | 72 wt. % |

In a kneader, APVA was dissolved under agitation in the given amount of pure water for ten minutes. After that, the given amount of "Siloide 978" powders was well kneaded with the resulting solution for 45 minutes to form a homogeneous paste.

| Material B: | |
|---|---|
| Crotonaldehyde | 5 wt. % |
| Succinic dihydrazide | 4 wt. % |
| Polyethylene-imine (with molecular weight of 10,000) | 4 wt. % |
| Finely divided silica ("Carplex 800", brandname, made by Fuji Davidson Kagaku K.K. and having a mean particle size of 2.5 μm and a pH value of 2.5) | 42 wt. % |
| Pure water | 45 wt. % |

In a kneader, the first three components above were dissolved under stirring in the given amount of pure water for 10 minutes. After that, the given amount of "Siloide 978" powders was well kneaded with the resulting solution for 60 minutes to form a homogeneous paste.

Materials A and B, each in a weighed amount of 10 g, were kneaded together for 10 seconds in a mixing machine. The resulting homogeneous paste gelated after eight minutes. The tensile strength was about 2.8 times as great as that of an alginate impression material. Following obtaining a mold with a glass plane, an α-type of gypsum ("New Plastone", brandname, made by GC Dental Industrial Corp.) was cast in the mold for setting. The set gypsum product was found to have a ten-point average surface roughness of 7.0 μm, indicating that the obtained gypsum surface was smoother than that of a control alginate impression material.

EXAMPLE 6

| Material A: | |
|---|---|
| APVA (having an acetoacetylation degree of 2 mol % and a polymerization degree of 100) | 4 wt. % |
| Finely divided silica ("Aerosil MOX80", brandname, made by Nippon Aerosil K.K. and having a mean particle size of 30 mμ and a pH value of 4.0) | 3 wt. % |
| Aluminium oxide ("Aluminium Oxide C", brandname, Nippon Aerosil K.K. and having a mean made by particle of 20 mμ and a pH value of 5.0) | 9 wt. % |
| Pure water | 84 wt. % |

In a kneader, APVA was dissolved under agitation in the given amount of pure water for 12 minutes. After that, the given amount of powders "Aerosil MOX80" and aluminium oxide was well kneaded with the resulting solution over 60 minutes to form a homogeneous paste.

| Material B: | |
|---|---|
| Adipic dihydrazide | 5 wt. % |
| Menthenediamine | 2 wt. % |
| L-arginine | 3 wt. % |
| Finely divided silica "Siloide 800", brandname, made by Fuji Davidson Kagaku K.K. And having a mean particle size of 2.7 μm and a pH value of 3.0) | 60 wt. % |
| Pure water | 30 wt. % |

In a kneader, the first three components above were dissolved under stirring in the given amount of pure water for 15 minutes. After that, the given amount of "Siloide 800" powders was well kneaded with the resulting solution for 60 minutes to form a homogeneous paste.

Materials A and B, each in a weighed amount of 10 g, were kneaded together for 10 seconds in a mixing machine. The resulting homogeneous paste gelated after eight minutes. The tensile strength was about 3.0 times as great as that of an alginate impression material. Following obtaining a mold with a glass plane, an α-type of gypsum ("New Plastone", brandname, made by GC Dental Industrial Corp.) was cast in the mold for setting. The set gypsum product was found to have a surface roughness of 6.2 μm, indicating that the obtained gypsum surface was smoother than that of a control alginate impression material.

EXAMPLE 7

| Material A: | |
|---|---|
| APVA (having an acetoacetylation degree of 14 mol. % and a polymerization degree of 500) | 8.5 wt. % |
| Finely divided silica ("Aerosil OX-50", brandname, made by Nippon Aerosil K.K. and having a mean particle size of 40 mμ and a pH value of 4.2) | 5.0 wt. % |
| Finely divided silica "Siloide 65", brandname, made by Fuji Davidson Kagaku K.K. and having a mean particle size of 3.5 μm and a pH value of 4.0) | 20.0 wt. % |
| Pure water | 66.5 wt. % |

In a kneader, APVA was dissolved under agitation in the given amount of pure water for 10 minutes. After that, the given amounts of "Aerosil OX-50" and "Siloide 65" powders were well kneaded with the resulting solution for 50 minutes to form a homogeneous paste.

| Material B: | |
|---|---|
| Carbodihydrazide | 8 wt. % |
| Finely divided silica ("Nipsil VN3", brandname, made by Nippon Silica K.K. and having a mean particle size of 17 mµ and a pH value of 6.0) | 6 wt. % |
| Finely divided silica "Siloide 800", brandname, made by Fuji Davidson Kagaku K.K. and having a mean particle size of 2.7 µm and a pH value of 3.0) | 25 wt. % |
| Pure water | 61 wt. % |

In a kneader, the carbohydrazide was dissolved under agitation in the given amount of pure water for 3 minutes. After that, the given amounts of "Nipsil VN3" and "Siloide 800" powders were well kneaded with the resulting solution for 60 minutes to form a uniform paste.

Materials A and B, each in a weighed amount of 10 g, were kneaded together for 30 seconds with a spatula. The resulting homogeneous paste gelated after seven minutes. The tensile strength was about 3.1 times as great as that of an alginate impression material. Following obtaining a mold with a glass plane, an α-type of gypsum ("New Plastone", brandname, made by GC Dental Industrial Corp.) was cast in the mold for setting. The set gypsum product was found to have a ten-point average surface roughness of 6.8 µm, indicating that the obtained gypsum surface was smoother than that of a control alginate impression material.

EXAMPLE 8

| Material A: | |
|---|---|
| APVA (having an acetoacetylation degree of 8 mol % and a polymerization degree of 200) | 3.5 wt. % |
| Finely divided silica ("Aerosil 380", brandname, made by Nippon Aerosil K.K. and having a mean particle size of 7 mµ and a pH value of 4.0) | 22.5 wt. % |
| Pure water | 74.0 wt. % |

In a kneader, APVA was dissolved under agitation in the given amount of pure water for 5 minutes. After that, the given amounts of "Aerosil 380" powders were well kneaded with the resulting solution for 60 minutes to form a homogeneous paste.

| Material B: | |
|---|---|
| Dialdehyde starch | 3 wt. % |
| Carbodihydrazide | 2 wt. % |
| Diethyltriamine | 4 wt. % |
| L-ornithine | 4 wt. % |
| Finely divided silica ("Nipsil 300", brandname, made by Nippon Silica K.K. and having a mean particle size of 4 mµ and a pH value of 6.0) | 10 wt. % |
| Finely divided silica ("Tokusil GU-N", brandname, made by Tokuyama Soda K.K. and having a mean particle size of 30 mµ and a pH value o 6.5) | 15 wt. % |
| Pure water | 62 wt. % |

In a kneader, the first four components above were dissolved under agitation in the given amount of pure water for 8 minutes. After that, the given amounts of "Nipsil 300" and "Tokusil GU-N" powders were well kneaded with the resulting solution for 60 minutes to form a uniform paste.

Materials A and B, each in a weighed amount of 10 g, were kneaded together for 40 seconds with a spatula. The resulting homogeneous paste gelated after 10 minutes. The tensile strength was about 2.9 times as great as that of an alginate impression material. Following obtaining a mold with a glass plane, an α-type of gypsum ("New Plastone", brandname, made by GC Dental Industrial Corp.) was cast in the mold for setting. The set gypsum product was found to have a ten-point average surface roughness of 7.2 µm, indicating that the obtained gypsum surface was smoother than that of a control alginate impression material.

Throughout the examples, the pHs of the fillers were measured in a 5% aqueous suspension with a pH meter.

COMPARATIVE EXAMPLE 1

| | |
|---|---|
| Sodium alginate | 14 wt. % |
| Dihydrous calcium sulfate | 15 wt. % |
| Trisodium phosphate | 3 wt. % |
| Diatomaceous earth | 65 wt. % |
| Sodium silicofluoride | 3 wt. % |

The above components were mixed together for 20 minutes in a blender. The resulting powder in a weighed amount of 16 g, was kneaded with 40 ml of water in a rubber bowl with an exclusive spatula for 30 seconds. The resulting homogeneous paste gelated after 3 minutes from the initiation of kneading. The tensile strength was 2.9 kg/cm$^2$. Following obtaining a mold with a glass plane, an α-type of gypsum ("New Plastone", brandname, made by GC Dental Industrial Corp.) was cast in the mold for setting. The set gypsum product was found to have a ten-point average surface roughness of 16.0 µm.

COMPARATIVE EXAMPLE 2

| | |
|---|---|
| Potassium alginate | 14.0 wt. % |
| Dihydrous calcium sulfate | 14.5 wt. % |
| Sodium pyrophosphate | 2.5 wt. % |
| Diatomaceous earth | 63.0 wt. % |
| Sodium fluoro titanate | 2.5 wt. % |

The above components were mixed together for 15 minutes in a blender. Blender mixing was further continued, during which a nonionic surfactant polyoxyethylene (20) sorbitan monolaurate (3.5 wt. %) were added dropwise.

The resulting powder, in a weighed amount of 16 g, were kneaded with 40 ml of water in a rubber bowl with an exclusive spatula for 30 seconds. The resulting homogeneous paste gelated after 3.5 minutes after the initiation of kneading. The tensile strength was 3.1 kg/cm$^2$. Following obtaining a mold with a glass plane, an α-type of gypsum ("New Plastone", brandname, made by GC Dental Industrial Corp.) was cast in the mold for setting. The set gypsum product was found to have a ten-point average surface roughness of 18.0 µm.

The impression materials according to the above-mentioned examples and the alginate impression materials according to the comparative examples were tested according to JIS T 6505 to measure their gelling time and measured in terms of tensile strength, dimensional changes in the air and ten-point average surface roughness of gypsum according to the following testing methods.

TABLE

| Items of Test Samples | Gelling Time | Tensile Strength (kg/cm²) | (After 1 hour) Dimensional Changes in Atmosphere (−%) | 10-Point Average Gypsum Surface Roughness (μm) |
| --- | --- | --- | --- | --- |
| Example 1 | 10' 00" | 8.5 | 1.5 | 7.5 |
| Example 2 | 8' 00" | 8.0 | 1.4 | 6.5 |
| Example 3 | 9' 00" | 7.2 | 1.5 | 6.0 |
| Example 4 | 10' 00" | 7.5 | 1.4 | 6.5 |
| Example 5 | 8' 00" | 8.1 | 1.3 | 7.0 |
| Example 6 | 8' 00" | 8.7 | 1.2 | 6.2 |
| Example 7 | 7' 00" | 9.0 | 1.3 | 6.8 |
| Example 8 | 10' 00" | 8.3 | 1.5 | 7.2 |
| Comparative Example 1 | 3' 30" | 2.9 | 3.2 | 16.0 |
| Comparative Example 2 | 3' 00" | 3.1 | 3.0 | 18.0 |

Tensile Strength

According to JIS K6301 "Tensile Testing", a dumbbelshaped specimen No. 2 was prepared. With an autograph (made by Shimadzu Corporation), this sample was pulled at its both ends until it was broken up, thereby determining its tensile strength at break.

Dimensional Change in the Air

According to the Standards of the American Dental Association, No. 19, a sample plate was prepared by kneading material at a room temperature of 23° C. and a humidity of 50% for 15 minutes and removing it from the mold. This sample was provided with two gauge marks. Subsequently, the distance between two gauge marks was measured with a gauge meter having 1/1000-mm accuracy (a comparator made by Shimadzu Corporation)—referred to as A. One hour later, it was again measured—referred to as B. Then, the dimensional change was found by the following equation:

$$\text{Dimensional Change (linear shrinkage)} = (A-B)/A \times 100.$$

Ten-Point Average Surface Roughness of Gypsum

According to JIS B0601, a mold with a glass plane was obtained. Hard gypsum ("New Plastone", brandname, made by GC Dental Industrial Corp. and coming up to JIS T6605) was poured onto the mold, followed by setting in an atmosphere of 100% humidity and, one hour later, the set sample was removed. After the lapse of one day, it was tested for its surface roughness with a measuring machine "Surfcorder SE-40H", brandname, made by Kosaka Kenkyusho.

From the results tabulated, it is noted that the alginate impression material of Comparative Example 1, which is generally used as a dental impression material, is likely to tear up due to its decreased tensile strength.

The comparative alginate impression materials undergo so large dimensional changes in the air that they shrink seriously upon exposed to the atmosphere. For this reason, hard gypsum must be poured in place just after impression-taking. Then, the resulting gypsum model is removed from the mold in an atmosphere of 100% humidity with as high precision as possible.

The gypsum surface roughness is unavoidably affected by gypsum cast in the comparative, gelled alginate impression materials, since the gypsum (dihydrous or hemihydrous calcium sulfate) serving as a model material is used as the gelling agent.

The novel aqueous impression materials according to this invention show a tensile strength about 2.5 to 3 times as great as that of the conventional alginate impression material; gelled APVA are unlikely to tear up. Their dimensional changes in the air are reduced to about ½ to ⅓ with improvements in dimensional precision; and the ten-point average surface roughness of gypsum is improved. It is thus possible to prepare gypsum models with high dimensional accuracy, which can provide an aqueous impression material having unprecedented properties.

Thus, the present invention provides an unprecedentedly novel aqueous impression material, the details of which are unlikely to tear up and which gives a gypsum model having a smooth surface and of high dimensional accuracy.

What is claimed is:

1. A dental impression composition which contains
    4 to 40% by weight of an acetoacetylated polyvinyl alcohol having an acetoacetylation degree of 0.5 to 15 mol % and a polymerization degree of 100 to 1,500,
    1 to 20% by weight of a gelling agent comprising one or more members selected from the group consisting of aldehyde, hydrazides and amines and
    20 to 85% by weight of fillers comprising one or more members selected from the group consisting of titanium oxide, silica, alumina and basic aluminum sulfate, all having a mean particle size of 1 mμ to 5 μm and a pH value of 7.0 or less.
2. A dental impression material which comprises
    material A formed of a paste containing
        2 to 20% by weight of an acetoacetylated polyvinyl alcohol having an acetoacetylation degree of 0.5 to 15 mol % and a polymerization degree of 100 to 1,500,
        5 to 60% by weight of filler comprising one or more members selected from the group consisting of titanium oxide, silica, alumina and basic aluminum sulfate, all having a mean particle size of 1 mμ to 5 μm and a pH value of 7.0 or less, and the balance being water, and
    material B formed of a paste containing
        0.5 to 15% by weight of a gelling agent comprising one or more members selected from the group consisting of aldehydes, hydrazides and amines,
        5 to 60% by weight of filler comprising one or more members selected from the group consisting of titanium oxide, silica, alumina and basic aluminum sulfate, all having a mean particle size of 1 mμ to 5 μm and a pH value of 7.0 or less, and the balance being water.
3. The dental impression composition according to claim 1 or 2, wherein said aldehydes are selected from the group consisting of acetaldehyde, propionaldehyde, crotonaldehyde, glyoxal, malondialdehyde, glutaraldehyde and dialdehyde starch.
4. The dental impression composition according to claim 1 or 3, wherein said hydrazides are selected from the group consisting of carbodihydrazide, oxalic dihydrazide, malonic dihydrazide, succinic dihydrazide, adipic dihydrazide, sebacic dihydrazide, dodecane dioic dihydrazide, isophthalic dihydrazide, terephthalic dihydrazide, glycolic dihydrazide and polyacrylic hydrazide.

5. The dental impression composition according to claim 1 or 2, wherein said amines are diamines.

6. The dental impression composition according to claim 1 or 2, wherein said amines are polyamines.

7. The dental impression composition according to claim 1 or 2, wherein said amines are amino acids.

8. The dental impression composition according to claim 1 or 2 wherein said amine is a polyethylene-imine having a molecular weight of 300 to 100,000 and represented by the following formula:

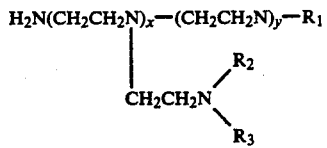

wherein $R_1$, $R_2$ and $R_3$ each stand for H or $CH_2CH_2NH_2$ and x and y are integers.

9. The dental impression composition according to claim 1 or 2 wherein said filler is selected from the group consisting of silica and basic aluminum sulfate.

* * * * *